(12) United States Patent
Heijkants et al.

(10) Patent No.: US 8,909,500 B2
(45) Date of Patent: Dec. 9, 2014

(54) MEASURING THE ANGLE BETWEEN A FIRST MEMBER AND A SECOND MEMBER UNDER DYNAMIC CONDITIONS

(75) Inventors: Ralf Guillaume Jean Catharina Heijkants, Eindhoven (NL); Caroline van der Horst, 's-Hertogenbosch (NL); Merijn Wijnen, Eindhoven (NL); Marcus Benedictus Hoppenbrouwers, Eindhoven (NL)

(73) Assignee: Nederlandse Organisatie voor toegepast-natuurwetenschappelijk onderzoek TNO (NL)

( * ) Notice: Subject to any disclaimer, the term of this patent is extended or adjusted under 35 U.S.C. 154(b) by 308 days.

(21) Appl. No.: 12/742,079

(22) PCT Filed: Nov. 3, 2008

(86) PCT No.: PCT/NL2008/050690
§ 371 (c)(1),
(2), (4) Date: Jul. 28, 2010

(87) PCT Pub. No.: WO2009/061181
PCT Pub. Date: May 14, 2009

(65) Prior Publication Data
US 2010/0286950 A1    Nov. 11, 2010

(30) Foreign Application Priority Data
Nov. 7, 2007  (EP) .................................... 07120195

(51) Int. Cl.
*A61B 5/00* (2006.01)
*G01B 11/26* (2006.01)
*A61B 5/107* (2006.01)

(52) U.S. Cl.
CPC ....... *A61B 5/1071* (2013.01); *A61B 2562/0219* (2013.01); *A61B 5/4528* (2013.01); *A61B 5/6828* (2013.01); *A61B 2562/028* (2013.01)
USPC ........................................................ 702/151

(58) Field of Classification Search
CPC ................ A61B 5/1071; A61B 5/1114; A61B 2562/028; A61B 2562/0219; G01B 11/26

USPC ......... 702/150; 73/514.35, 514.36; 250/227.3
See application file for complete search history.

(56) References Cited

U.S. PATENT DOCUMENTS 4,542,291 A    9/1985  Zimmerman
(Continued)

FOREIGN PATENT DOCUMENTS

CA    2 241 359 A1    12/1999
CA    2241359 A1  *  12/1999

OTHER PUBLICATIONS

Lee et al. Wearable Master Device Using Optical Fiber Curvature Sensors for the Disabled, IEEE, 2001, pp. 892-896.*

(Continued)

*Primary Examiner* — Eliseo Ramos Feliciano
*Assistant Examiner* — Michael Dalbo
(74) *Attorney, Agent, or Firm* — Knobbe Martens Olson & Bear LLP

(57) ABSTRACT

Method and system for measuring an angle between a first member and a second member under dynamic conditions is provided. A first and second acceleration sensor and an angle measuring device (goniometer) are connected to the first and second member. Under dynamic and static conditions, the angle ($\alpha$) is measured by the goniometer. Under static conditions, the inclination angle of the first member is measured using the first acceleration sensor and the inclination angle of the second member using the second acceleration sensor and the angle ($\alpha'$) between the first and second members is calculated. Then the deviation is calculated between the angle ($\alpha$) and the angle ($\alpha'$). An error correction factor is calculated from the deviation between both angles ($\alpha,\alpha'$). The error correction factor is applied to future and/or previous measurements of the angle ($\alpha$) between the first and second member done by the goniometer.

9 Claims, 2 Drawing Sheets

(56) References Cited

U.S. PATENT DOCUMENTS

2006/0043293 A1\* 3/2006 Doi et al. .................. 250/310
2008/0154098 A1\* 6/2008 Morris et al. ............... 600/300
2009/0044593 A1\* 2/2009 Stormbom et al. ........... 73/1.06

OTHER PUBLICATIONS

Louis, V., et al. "Optical fiber based sensor for angular measurement in rehabilitation." Systems, Man and Cybernetics, 1993.'Systems Engineering in the Service of Humans', Conference Proceedings., International Conference on. IEEE, 1993.\*

International Search Report issued in PCT/NL2008/050690 dated Feb. 12, 2009.

Williamson R. et al., Detecting absolute human knee angle and angular velocity using accelerometers and rate gyroscopes, Medical and Biological Engineering and Computing, vol. 39, No. 3, pp. 294-302, May 2001.

\* cited by examiner

MEASURING THE ANGLE BETWEEN A FIRST MEMBER AND A SECOND MEMBER UNDER DYNAMIC CONDITIONS

This application is the U.S. National Phase of International Application No. PCT/NL2008/050690, filed Nov. 3, 2008, designating the U.S. and published in English as WO 2009/061181 on May 14, 2009 which claims the benefit of European Patent Application No. 07120195.8 filed Nov. 7, 2007.

FIELD OF THE INVENTION

The invention relates to measuring the angle between a first member and a second member under dynamic conditions, i.e. when the first and/or second members are in motion. One aspect is to provide a method for measuring the angle between a first member and a second member under dynamic conditions. Another aspect is to provide a measurement system which is arranged for performing such a method. Yet another aspect is to provide a system for monitoring angle variations between e.g pivoting limbs of humans or animals, e.g. knee joints etc. under live conditions, e.g. for scientific or therapeutic reasons.

BACKGROUND

Measuring the angle between a first member and a second member under dynamic conditions may be useful e.g. for monitoring angle variations between pivoting limbs of humans or animals, e.g. knee joints etc., under live conditions, e.g. for scientific or therapeutic reasons. Such measuring method or system has to be robust and rather insensitive for differences in the way the system is attached to those joints, e.g. by means of a flexible connection brace.

Goniometers, capable to output a measuring value in dependency of the angle between the first and second member are known per se. U.S. Pat. No. 4,542,291 discloses a goniometer, in which an optical flex sensor is provided comprising a flexible tube having two ends, a reflective interior wall within the flexible tube, a light source placed within one end of the flexible tube and a photosensitive detector placed within the other end of the flexible tube to detect a combination of direct light rays and reflected rays when the flexible tube is bent.

Other types of optical fiber type sensors for use as a goniometer are e.g. known as such from the prior art, including an imperfected graded-index. plastic optical fiber as a deformation sensor having good sensing characteristics.

This optical fiber bending sensor and other optical fiber bending sensors are also listed in an article titled A New Flexible Optical Fiber Goniometer for Dynamic Angular Measurements: Application to Human Joint Movement Monitoring by Donno, M.; Palange, E.; Di Nicola, F.; Bucci, G.; Ciancetta, F. in Instrumentation and Measurement, IEEE Transactions on Volume 57, Issue 8, Aug. 2008 Page(s):1614-1620 (reference 2 in the following). For instance, reference 2 shows the application of an optical fiber bending sensor in a joint angle sensor, the sensor being attached to an elbow by means of one or two braces.

Canadian patent application No CA 2241359 discloses a goniometer that uses angular rate sensors, such as rate gyroscopes placed on different limbs. In this case the angle is determined by integration of the angular rate. This document notes that this may lead to a drifting angle. In order to reduce drift an accelerometer is added, which is used to reset the gyroscope angle. A similar solution is described in an article titled "Detecting absolute human knee angle and angular velocity using accelerometers and rat gyroscopes", by R. Williamson et al., published in Medical and Biological Engineering & Computing 2001, Vol. 39 pages 294-302 (EPO referenceXP001178743).

It has been found that angle measuring results from the goniometer (e.g. fiber or flexible tube type) may give less reliable measuring results due to the way it has been attached to the relevant joint, e.g. by means of one or two flexible braces. Besides that the goniometer may not have been installed quite correct initially, the goniometer (i.e. its attachments points) may, moreover, shift somewhat to and fro over the limbs, due to the flexible nature of the brace(s) and the skin of the human or annual.

SUMMARY

Among others an aspect is to provide an angle measuring system which is very robust and rather insensitive for differences in the way the system is attached to joints.

Among others, an aspect is to provide automatic calibration of the system during static moments or periods, i.e. when the first and second members are in rest.

Any type of goniometer, capable to output a measuring value in dependency of the angle between the first and second member, may be used as an angle measuring device. It may, however, be preferred to use an optical fiber type sensor.

The present invention is based at the understanding that the robustness of the measuring method or system can be substantially be improved by initial calibration factor (or correction) and, preferably, periodical recalibration of the angle measuring results from the (e.g. fiber or flexible tube type) goniometer. To improve the system's accuracy, the (additional) use of acceleration or inclination sensors is proposed to provide automatic calibration of the means for dynamic angle measurement, i.e. the goniometer, viz. during static moments or periods, i.e. when the first and second members are in rest (initially and/or during operation).

According to the invention it is preferred to perform next steps for measuring the angle between a first member and a second member under dynamic conditions:

connect an angle measuring device (goniometer) to the first and the second member, which angle measuring device is arranged for measuring the angle between the first and second member under static and under dynamic conditions;

connect a first acceleration sensor to the first member and connect a second acceleration sensor to the second member;

under dynamic conditions,
    measure the angle between the first and second member by means of the angle measuring device;

under static conditions,
    measure the angle between the first and second member by means of the angle measuring device;
    measure the inclination angle of the first member using the first acceleration sensor and the inclination angle of the second member using the second acceleration sensor and calculate the angle between the first and second member;
    calculate the deviation between the angle between the first and second member as measured by the angle measuring device and the angle between the first and second member as calculated from the inclination angle of the first member as measured by the first acceleration sensor and the inclination angle of the second member as measured by the second acceleration sensor;
    calculate an error correction factor from said deviation between the angle between the first and second member as measured by the angle measuring device and the angle between the first and second member as calculated from the inclination angle of the first member as measured by the first acceleration sensor and the inclination angle of the second member as measured by the second acceleration sensor;

apply said error correction factor to future (and/or previous) measurements of the angle between the first and second member by means of the angle measuring device.

BRIEF DESCRIPTION OF THE DRAWING

These and other advantageous aspects will become apparent from a description of an exemplary embodiment of the invention, referencing to FIG. 1, which shows a goniometer system placed on a knee FIG. 2, which shows a schematic of a goniometer system

DETAILED DESCRIPTION OF AN EXEMPLARY EMBODIMENT

Figure 1:
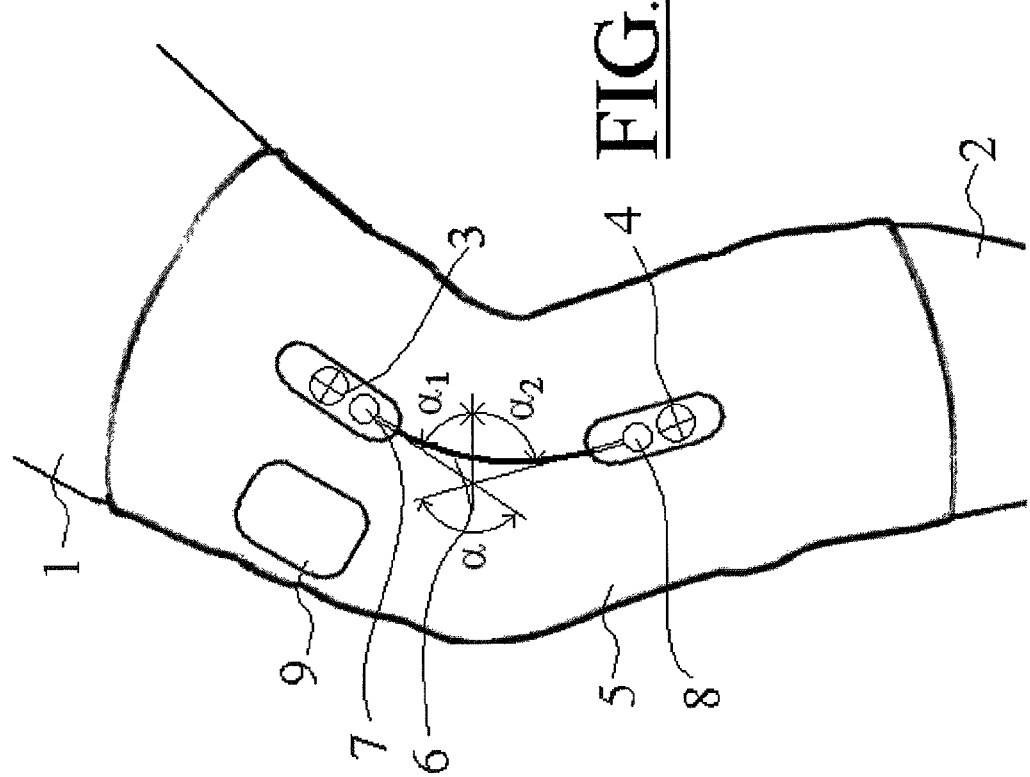

FIG. 1 shows an exemplary embodiment of a system which is fit for performing the method as outlined above for measuring the angle between a first member 1 and a second member 2 under dynamic conditions.

Figure 2:
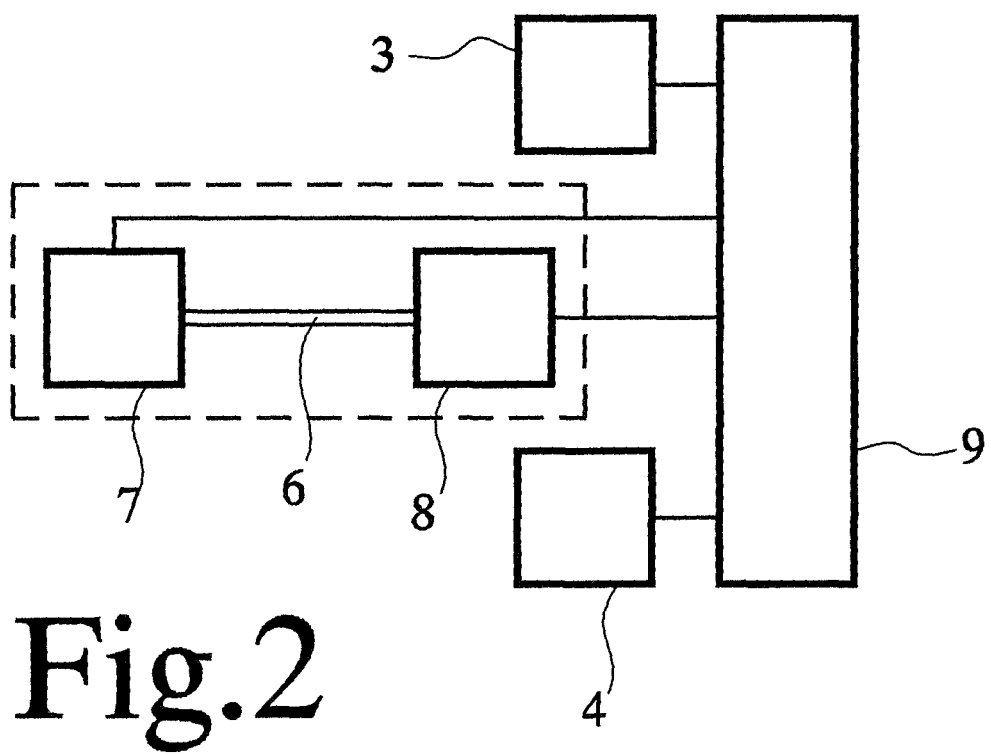

FIG. 2 shows a schematic of the system comprising a first acceleration sensor 3, a second acceleration sensor 4, an angle measuring device 6 and a processing module 9. First acceleration sensor 3, second acceleration sensor 4 and an angle measuring device 6 are coupled to processing module 9. The angle measuring device is implemented as a flexible fiber or thin tube 6 (see references above), as well as a light source 7 at one end of the wire/tube and a light detector 8 at the other end. Light source 7 and light detector 8 are coupled to processing module 9.

A first acceleration sensor 3 is connected to the first member 1, in this case the upper part of a leg, and a second acceleration sensor 4 to the second member 4, the lower part of the leg, by means of a knee brace 5.

Further, an angle measuring device 6 is connected to the first and the second member 1, 2, viz. integrated in the brace 5. In this embodiment the device comprises a flexible fiber or thin tube 6 (see references above), as well as a light source 7 at one end of the wire/tube and a light detector S at the other end. The light source 7 and the light detector 8 may be located at the same member 1 or 2, as suggested by reference 3 (the wire/tube having the shape of a stretched loop extending over de joint) or being located on both sides of the connection joint of members 1 and 2. Both are connected to a processing module 9, which is enabled to calculate, from the ratio between the power entered into the light source 7 and the power received by the light detector 8, an angle $\alpha_{static}$ between the first and second member. Calculating the value of $\alpha_{static}$ from said power ratio is deemed to be within the capabilities of any person skilled in the art being aware of e.g. the prior-art disclosed in the above references.

All sensors 3, 4, 7 and 8 are connected to module 9 via a (not shown) wiring attached to or integrated in the knee brace 5. The processing could be performed locally, in processing module 9. It may, however, be preferred that the actual processing is performed in remote processing means, e.g. a dedicated processor or a PC loaded with a (software) control and/or processing module. In that case the module 9 can be considered as a virtual processing module, which may mainly comprise a communication interface, fit to transmit—wireless or wired—the relevant input and output signals between the components 3, 4, 7 and 8 and a communication interface at the side of the remote processor or PC. For the sake of simplicity, however, module 9 will be considered hereinafter as the system's processing module 9, either substantially or at least partly using remote processing capacity or substantially or at least partly using its own processing capacity. The processing module 9 may, via relevant communication interfaces, be controlled, activated, set, read out etc., via wired or wireless communication, by means of e.g. a remote control unit or a PC loaded with relevant activation and/or control software.

After the knee brace 5 has been installed the processing module 9 is activated to measure, under static condition, i.e. during rest of the upper leg 1 and lower leg 2, the inclination angle $\alpha_{static}1$ of the first member 1 (the upper leg) using the first acceleration sensor 3, as well as the inclination angle $\alpha_{static}2$ of the second member 2 (the under leg) using the second acceleration sensor 4, and to calculate the angle $\alpha_{static}=\alpha_{static}1-\alpha_{static}2$.

The processing module 9, moreover, is activated to measure the (same) angle between the first and second member by means of the angle measuring device 6-8, i.e. the optical fiber goniometer, and to compute, from the ratio of the input power (of the signal to the light source 7) and the power output (of the signal from the light detector 8), the angle between the upper leg 1 and the lower leg 2, resulting in a calculation result $\alpha_{static}'$.

Next the processing module 9 calculates and stores an angle error correction factor c from $c=\alpha_{static}-\alpha_{static}'$ or $c=\alpha_{static}/\alpha_{static}'$, which correction factor c must be applied to future angle measurements performed by the angle measuring device (fiber goniometer) 6-8.

Under a dynamic condition following the static (rest) condition, during which the error correction factor was calculated and stored, (the dynamic and static conditions can simply be detected by the acceleration sensors 3, 4, which, after all, are acceleration sensors, which are able to detect any motions of the upper leg 1 and/or the lower leg 2), the processing module 9 is instructed to measure all occurring angle values $\alpha_{dynamic}$, using (only) the goniometer 6-8. The measuring results, i.e. the measured angle values, may be registered in (or via) the processing module 9 or be sent directly to a remote control device, however, after being corrected by the error correction factor c, which was calculated during the last static (rest) period.

Each time the upper leg 1 and lower leg 2 return into a static condition, i.e. the leg parts 1 and 2 are in rest for some time (detected by the accelerator sensors 3 and 4 together with the processing module 9) the calibration procedure may be repeated by measuring again the values for $\alpha_{static}$ (measured by the goniometer 6-8) and $\alpha_{static}'$ (measured by the accelerator sensors 3,4) and recalculating the error correction factor c to be used during the dynamic condition(s) following that (temporary) static condition.

In this way a method and system is provided for measuring the angle between the first member I and the second member 2, e.g. pivoting limbs of humans or animals, e.g. knee joints etc. under dynamic (live) conditions, which is very robust and rather insensitive for differences in die way the system is attached to those joints, e.g. by means of the flexible connection brace 5. During static moments or periods, i.e. when the first and second members are in rest, automatic (re)calibration of the means for dynamic angle measurement, i.e. the fiber type goniometer 6-8, is performed by calculating a correction factor c ($c=\alpha_{static}-\alpha_{static}'$ or $c=\alpha_{static}/\alpha_{static}'$) which is registered into the processing module 9 and with which the angle measured by the goniometer 6-8 ($\alpha$) is corrected, by the processing module 9, during the next dynamic measurements, e.g. before outputting and/or further processing.

Additionally, or instead, (some) previous angle measurements of the goniometer 6-8 (α) may be stored in the processing module 9 and corrected retroactively, e.g. before outputting and/or further processing.

Thus the method and system according to the invention will result in more reliable results in testing under live conditions, e.g. in scientific or therapeutic environments.

Acceleration sensors are sensors that measure at least the direction and optionally the size of the accelerating force to which objects are subjected, such as the force of gravity. Acceleration sensors are generally known as such e.g. in the form of rather simple micro electro-mechanical system (MEMS) devices, sometimes consisting of little more than a suspended cantilever beam or test mass (also known as seismic mass) with some type of deflection sensing and circuitry. That is, an embodiment of acceleration sensors may measure displacement of a test mass due to the influence of the force of gravity. This type of acceleration sensor has been incorporated in e.g. personal electronic devices such as media players, handheld gaming devices etc. Acceleration sensors are capable to determine their inclination angle w.r.t. the direction of the gravitation field; acceleration sensors thus may be used as inclination sensors.

However, due to several different accelerations which may occur under dynamic conditions, such acceleration sensors are not suitable as inclination sensors under dynamic conditions. Under static conditions (only then), the angle between a first and a second member thus could be calculated by measuring the inclination angle (i.e. the angle to the direction gravitation field) of the first member using the first acceleration sensor and the inclination angle of the second member using the second acceleration sensor. A small processor could be used to calculate the mutual angle between both members.

Thus, although such accelerator sensors are not suitable for inclination measurement of members or limbs under dynamic conditions (i.e. the members/limbs being in motion), they are under static conditions (i.e. the members/limbs being in rest). Besides, the angle measurement is more robust and less sensitive for displacements of the sensors than the optical fiber/tube type sensors are. The present invention makes use of that property by measuring (under dynamic and static conditions) the mutual angle between the first and second members by means of a state-of-the-art goniometer which, however, may be somewhat inaccurate due to the not highly accurate and reliable attachment of the sensor parts to the members (e.g. by means of a brace), and by calibrating/correcting the measuring results from the goniometer during periods when the members are in rest, viz. by means of a couple of accelerator sensors, the measurement results of which are considered more reliable due to the nature of such accelerator sensors.

Although an example has been shown wherein the knee bending angle is measured, between the thigh and the lower leg, it should be appreciated that other angles may be measured in a similar way. Any kind of angle differences in a plane of rotation perpendicular to a rotation axis may be measured. For example bending angles between different limbs may be measured, where the rotation axis is substantially perpendicular to the limbs or relative torsion angles, where the rotation axis is substantially parallel to the limbs or body parts that rotate relative to each other.

What is claimed is:

1. A method of measuring an angle (α) between a first member and a second member under dynamic conditions, comprising:
   connecting a first acceleration sensor to the first member and connecting a second acceleration sensor to the second member;
   connecting an angle measuring device to the first and the second members, wherein the angle measuring device is configured to measure, under static and dynamic conditions, a measuring value dependent on the angle (α) between the first and second members;
   wherein the angle measuring device is a flexible goniometer which measures the angle between the members directly;
   under dynamic conditions,
   measuring the angle (α) between the first and second members by the angle measuring device;
   under static conditions,
   measuring an angle (αstatic) between the first and second members by the angle measuring device;
   measuring the inclination angle of the first member using the first acceleration sensor and the inclination angle of the second member using the second acceleration sensor and calculating an angle (αstatic') between the first and second members;
   calculating a ratio between the angle (αstatic) between the first and second members as measured by the angle measuring device and the angle (αstatic') between the first and second members as calculated from the inclination angle of the first member as measured by the first acceleration sensor and the inclination angle of the second member as measured by the second acceleration sensor;
   calculating an error correction factor from said ratio between the angle (αstatic) between the first and second members as measured by the angle measuring device and the angle (αstatic') between the first and second members as calculated from the inclination angle of the first member as measured by the first acceleration sensor and the inclination angle of the second member as measured by the second acceleration sensor; and
   applying said error correction factor to future and/or previous measurements of the angle (α) between the first and second members by the angle measuring device.

2. A method according to claim 1, wherein the angle measuring device is an optical fiber flex sensor, comprising a fiber attached to said first and second members.

3. A method according to claim 1, wherein the angle measuring device comprises as a flexible fiber or thin tube, with first and second ends attached to respective ones of the first and second members, a light source at the first end of the wire or tube and a light detector at the second end of the wire or tube opposite the first end.

4. A method according to claim 1, further comprising:
   detecting, by at least one of the first and second acceleration sensors, a change from one of the static conditions to one of the dynamic conditions following said static condition,
   wherein the angle (α) between the first and second members is measured by the angle measuring device upon detection of the change from said static condition to said dynamic condition,
   wherein said error correction factor is obtained during said static condition and applied to the angle (α) between the first and second members measured during said dynamic condition.

5. A system for measuring an angle between a first member and a second member under dynamic conditions, the system comprising:
   an angle measuring device configured to measure, under static and dynamic conditions, a measuring value dependent on the angle (α) between the first and second members;

wherein the angle measuring device is a flexible goniometer which measures the angle between the members directly;

a first acceleration sensor and a second acceleration sensor, each of which is coupled to the first member and the second member, respectively; and a processing module coupled to the angle measuring device and the first and second acceleration sensors, wherein the processing module is configured to obtain a measurement of the angle between the first and second members by the angle measuring device under dynamic conditions and to apply an error correction factor to the measurement of the angle; and wherein, under static conditions, the processing module is configured to:

obtain a further measurement of the angle between the first and second members by the angle measuring device;

obtain measurements of a first inclination angle of the first member using the first acceleration sensor and a second inclination angle of the second member using the second acceleration sensor and calculate a difference angle between the first and second members from the measurements of the first and second inclination angles;

calculate a ratio between the further measurement of the angle and the difference angle; and calculate the error correction factor from said ratio.

6. A system according to claim 5, wherein each of the first and second acceleration sensors comprises:

a cantilever beam or a test mass; and a deflection sensor.

7. A system according to claim 5, wherein the angle measuring device is an optical fiber flex sensor comprising a fiber configured to be attached to said first and second members.

8. A system according to claim 5, wherein the angle measuring device comprises a flexible fiber or thin tube with a first end and a second end configured to be attached to respective ends of the first and second members, a light source at the first end of the wire or tube, and a light detector at the second end of the wire or tube, opposite the first end.

9. A non-transitory computer program product, comprising a program of instructions that, when executed by a programmable computer, cause the computer to determine an angle between a first member and a second member using steps of:

receiving a measurement of an angle between a first member and a second member by an angle measuring device under dynamic conditions, wherein the angle measuring device is configured to measure, under static and dynamic conditions, a measuring value dependent on the angle ($\alpha$) between the first and second members;

wherein the angle measuring device is a flexible goniometer which measures the angle between the members directly; and under static conditions, receiving a further measurement of the angle between the first and second members by the angle measuring device;

receiving measurements of a first inclination angle of the first member using a first acceleration sensor and a second inclination angle of the second member using a second acceleration sensor;

calculating a difference angle between the first and second members from the measurements of the first and second inclination angles;

calculating a ratio between the further measurement of the angle and the difference angle;

calculating an error correction factor from said ratio; and applying said error correction factor to future and/or previous measurements of the angle between the first and second members by the angle measuring device.

* * * * *